United States Patent [19]

Wren

[11] Patent Number: 5,238,685
[45] Date of Patent: Aug. 24, 1993

[54] WOUND DRESSING

[75] Inventor: David C. Wren, Hindhead, United Kingdom

[73] Assignee: BritCair Limited, Aldershot, England

[21] Appl. No.: 810,269

[22] Filed: Dec. 19, 1991

Related U.S. Application Data

[63] Continuation of Ser. No. 662,299, Feb. 28, 1991, abandoned.

[30] Foreign Application Priority Data

Aug. 31, 1989 [GB] United Kingdom ............... 8820564

[51] Int. Cl.$^5$ .............................................. A61L 15/00
[52] U.S. Cl. .................................... 424/445; 424/443; 424/447
[58] Field of Search .................. 424/445, 447, 443

[56] References Cited

U.S. PATENT DOCUMENTS

| | | | |
|---|---|---|---|
| 3,824,997 | 7/1974 | Franklin | 424/443 |
| 4,199,644 | 4/1980 | Platt | 428/300 |
| 4,793,337 | 12/1988 | Freeman | 428/284 |
| 4,851,394 | 7/1989 | Kubodera | 536/1.1 |
| 4,948,575 | 8/1990 | Cole | 424/44 |

FOREIGN PATENT DOCUMENTS

| | | |
|---|---|---|
| 0243069 | 10/1987 | European Pat. Off. . |
| 279118 | 8/1988 | European Pat. Off. . |
| 0344913 | 6/1989 | European Pat. Off. . |
| 415042 | 8/1934 | United Kingdom . |
| 568177 | 3/1945 | United Kingdom . |
| 653341 | 5/1951 | United Kingdom . |
| 1231506 | 5/1971 | United Kingdom . |
| 1280631 | 7/1972 | United Kingdom . |
| 1394741 | 5/1975 | United Kingdom . |
| 8900706 | 12/1989 | United Kingdom . |
| 8403705 | 9/1984 | World Int. Prop. O. . |

*Primary Examiner*—Thurman K. Page
*Assistant Examiner*—D. Gabrielle Phelan
*Attorney, Agent, or Firm*—Charles M. Caruso; Richard S. Parr

[57] ABSTRACT

A wound dressing comprises a backing layer, which is preferably a semi-permeable material, and a wound contact pad. The wound contact pad comprises a mixed salt alginate, preferably in the form of fibres, which have first and second cations. The first cation (which may be calcium) is capable of forming an insoluble alginate salt and the second cation (which may be sodium) is capable of forming a soluble alginate salt. The equivalent ratio of the first to second cations is from 40:60 to 90:10, and is preferably about 80:20. Such dressings are useful in wound management, as the mixed salt alginate is particularly efficacious in combination with a backing layer.

6 Claims, No Drawings

WOUND DRESSING

This is a continuation of U.S. application Ser. No. 662,299, filed Feb. 28, 1991, now abandoned.

This invention relates to dressings for wounds for the human or animal body. More particularly, the invention relates to wound dressings incorporating alginate fibres. The term "wound dressing" as used in this specification includes surgical dressings. The term "wound" includes burn, cut, sore, blister, rash or any other lesion or area of troubled skin.

Certain alginate fibres have been known for use in surgical dressings for some time. GB-A-0653341 is an example of an early disclosure of the use of calcium alginate materials in surgical dressings. The earliest such materials were calcium alginate fibres, but they suffered from the disadvantage of being quite insoluble in water or wound exudate matter. Accordingly, it was proposed to replace a proportion of the calcium ions in calcium alginate with other cations, whose alginate salts are soluble. Bonniksen in GB-A-0653341 therefore proposed that some of the calcium ions be replaced with sodium ions, in a process which has come to be known as "conversion" of calcium alginate to form a mixed salt alginate.

The manner in which conversion took place then received attention from various groups of workers, as can be seen in GB-A-1231506 and GB-A-1394741. It appears that that there was some belief that alginates in which the calcium alginate fibres were converted to a 50:50 Ca:Na mixed salt fibre (on an equivalent basis) promoted haemostasis. It seems that haemostasis was believed to be closely linked with the property of solubility, which increased with the proportion of solubilising (for example sodium) ions. It is now believed that the property of haemostasis is not wholly attributable to dissolution.

Although the 50:50 Ca:Na mixed salt fibre was popular, it became difficult to handle when in contact with liquid wound exudate material, precisely because of the solubility that made it apparently desirable: the partially soluble 50:50 calcium:sodium mixed salt alginate fibres swell on contact with water and aqueous media to produce a gel-like slab.

Modern theories of wound management are based upon controlling the environment adjacent to the wound while at the same time preventing or reducing the ingress of dirt and bacteria and preventing or reducing the likelihood of physical damage to the healing surfaces. To this end, known wound dressings comprise a banking layer and a wound contact pad which is generally made of cotton.

EP-A-0243069 discloses a wound dressing in which the wound contact pad is formed from an alginate. The only wound contact pad specifically exemplified is formed of calcium alginate fibres.

It has now been found that certain alginate materials, especially fibres, having particular ratios of cations can be used to form particularly useful wound contact pads in wound dressings, particularly when the backing layer of the wound dressing comprises a semi-permeable film.

According to a first aspect of the present invention, there is provided a wound dressing comprising a backing layer and a wound contact pad, wherein the wound contact pad comprises a mixed salt alginate which has first and second cations, the first cation being capable of forming an insoluble alginate salt and the second cation being capable of forming a soluble alginate salt, the equivalent ratio of the first to second cations being from 40:60 to 90:10.

It has been found, that in the context of a wound dressing as described above, a mixed salt alginate having cation ratios in the above range exhibits a highly effective combination of properties. There is sufficient insolubilising cation in the mixed salt alginate for the wound contact pad to be relatively easy to be manipulated, even when wet with wound exudate, and there is sufficient solubilising cation for the wound contact pad to be soft, easy to remove and to be capable of removing unwanted fluid from the wound.

The alginate preferably comprises mixed salt alginate fibres, although under some circumstances alginate gels, powders or films may be useful.

It is preferred that the ratio of first (insolubilising) cation to second (solubilising) cation lie in the range of from 60:40 or 70:30 to 85:15. An 80:20 ratio has been found to be the most preferred.

Calcium is the preferred first cation, not least because calcium ions which are gradually liberated from the wound contact pad into the wound, in use of the dressing, are believed to have a haemostatic effect. Other suitable first cations include zinc. The preferred second cation is sodium, because sodium alginate is readily soluble. However, any other cation whose alginate salt is soluble could be used; examples include potassium, lithium, ammonium and magnesium. It will generally be the case that there will only be two species of cations present in the mixed salt alginate fibre, but this is not necessarily the case. Other cations, such as hydrogen ions, may be present.

The wound contact pad may contain some fibres or other alginic material which are insoluble. An example of an insoluble fibre is a calcium alginate fibre of a high calcium content. The combination of soluble and insoluble fibres may give a combination of rapid gelling with a particularly stable fibre structure, enabling the wound contact pad readily to be completely removed from the wound after treatment. It should be noted that it is not necessary for the insoluble fibres or other material to be alginate: they could be any insoluble fibres or material which does not have an adverse effect on the wound under the prevailing conditions.

The pad will generally be provided in the form of a sheet. Because of the properties of the second (solubilising) cation, the sheet will tend to acquire certain gel-like qualities on contact with wound exudate. The sheet may be non-woven, woven or knitted.

It is particularly preferred for the sheet to be non-woven, not only for ease of manufacture but also because of the general dimensional stability of non-woven fabrics: they tend not to stretch so easily as knitted fabrics.

The preferred sheet of alginate fibres which goes to form the pad is generally formed by converting a sheet formed from insoluble fibres. However, insoluble fibres could first be converted and then the converted fibres could be formed into a sheet or other pad. For ease of handling during sheet or pad formation, it is generally preferred to leave the conversion until afterwards.

Insoluble alginate fibres, in the form of calcium alginate fibres, may be prepared by the method of Bonniksen as disclosed in GB-A-0415042 and the method of Tallis as disclosed in GB-A-0568177. The calcium (or other insolubilising cation) fibres thus prepared can then be converted or, for preference, formed into a sheet or other piece of fabric. If a non-woven fabric is to be prepared, and this is the fabric of choice, a cotton card may be used to form a web, which may then be cross-lapped, for example with a Garnet Bywater cross-lapper and then needle punched in a Garnet Bywater needle loom.

If a woven fabric is to be prepared, the calcium (or other insoluble) alginate fibres may be carded and then spun into a yarn, which can be woven in a conventional loom. Alternatively, the fibres may be collected in a spinning box, according to the method of Tallis (GB-A-0568177) and woven. If a knitted fabric is to be prepared, the fibres can be prepared as a continuous filament yarn (again according to the method of Tallis (GB-A-0568177)), which is then knitted on a conventional knitting machine.

Various conversion methods, to replace some of the calcium or other insolubilising cations with sodium or other solubilising cations, can be used either on a tow of fibres prior to fabric preparation or on a fabric prepared from such fibres. First, the technology as developed by Miller and Caldwell (GB-A-1231506) may be used. In one embodiment of this technique, fibres or fabric of calcium (or other insolubilising cation) alginate and water are put into a dyeing machine. Sufficient hydrochloric acid to remove the desired percentage of insolubilising cation is introduced and circulated for 30 minutes. The liquid is drained and the fibres or fabric are then washed with water until no more acidity is detectable in the wash water. The dyeing machine is then charged with 50% w/w industrial methylated spirits (IMS) in water. The hydroxide of the desired solubilising cation (for example caustic soda) is then added. In the case of caustic soda, this should be done very slowly and with circulation. Care should be taken that the pH never exceeds 10. The amount of hydroxide added should be sufficient to neutralise the acid groups on the yarn; the system is recirculated until all the hydroxide has been used. The machine is then drained and the fabric or fibres washed in 50% IMS in water. The fabric or fibres are then transferred to a centrifuge and spun dry, and then air dried at a temperature of from 30° to 40° C.

A different conversion method that can be used is the method disclosed in GB-A-1394741 (Medical Alginates), an embodiment of which can also use a dyeing machine or even a stainless steel washing machine. Example 12 of GB-A-1394741 illustrates a suitable embodiment in general terms for converting calcium alginate fibres to calcium:sodium mixed salt fibres. The quantity of sodium acetate trihydrate used is varied according to the desired resulting proportion of sodium ions. 4% w/v sodium acetate, calculated as the anhydride, would be used to obtain 80:20 calcium:sodium alginate; this would approximate to about 6.6 kg of sodium acetate trihydrate in 100 dm$^3$ of liquor.

A further conversion method which can be used is disclosed in WO-A-8403705 (Courtaulds).

As with the fabric preparation methods, the conversion methods given above are purely illustrative, and it is to be emphasised that any suitable conversion method can be used.

The alginate is preferably derived from *Laminaria hyperborea* or any other suitable source. The ratio of guluronate/mannuronate residues may range from 1.5:1 to 2.5:1, preferably from 1.75:1 to 2.4:1 and may be about 2:1 or 2.3:1.

The pad may include one or more antimicrobial (for example antibacterial or antifungal) agents and/or one or more local anesthetics (for example novocain) and additionally or alternatively one or more pharmaceutical agents.

The backing layer may be adhesive coated or otherwise provided with adhesive means to allow adhesion of the dressing in the area of the wound. Adhesive means can also be used to keep the wound contact pad in place on the backing layer. To achieve all these purposes, it is most convenient to coat the backing layer with a layer of adhesive, which should usually be hypoallergenic. One or more antiseptics, astringents and/or topical protectants may be incorporated in the adhesive layer.

The backing layer may be a fabric, in which case it can be non-woven, woven or knitted. As an alternative, the backing may be made of plastics material, for example a substantially continuous plastic hypoallergenic film. The backing layer may include or be constituted by a resilient layer, for example, plastics foam layer, to assist in the protection of, and prevention of damage, to the wound.

The backing layer may be permeable, semi-permeable or impermeable. It is particularly preferred for the backing layer to be a semi-permeable material, such as is disclosed in GB-A-1280631. Such a backing layer includes adhesive, which serves both to cause the pad to adhere to the backing layer and to cause the dressing to adhere to the wound area. It is therefore preferred that the backing layer be a moisture vapour permeable pressure sensitive adhesive material for use on animal skin and nails, comprising a backing material having a pressure sensitive adhesive on at least substantially the whole of the body-adhering portion for at least one surface of the said backing material, both said backing material and said adhesive being moisture vapour permeable and unaffected by water and at least one of said backing material and said adhesive comprising a synthetic polymer and being continuous and non-permeable to liquid water, said adhesive material having a moisture vapour permeability of at least 300 g per square meter per 24 hours per 40° C. per 80% relative humidity. The preferred features disclosed in GB-A-1280631 constitute preferred features of the backing layer of wound dressings according to this invention.

It can be seen that at least some of the embodiments of the invention have a number of particular advantages for wound management. A sealed environment can be provided around the wound; dressings according to the invention can control the water vapour and oxygen flow to and from the wound; they can thermally insulate and mechanically protect the wound; they do not shed large quantities of hydrocolloid material into the wound; they are not excessively adherent; they contain in the dressing face only materials which are fully biodegraded in the wound; they hold the exudate from the wound so that a cleaner wound may be obtained; and they donate calcium ions which are believed to promote wound healing.

Dressings in accordance with the invention may be strip dressings, in which the wound contact pad forms a (usually centrally located) strip on the backing layer. However, advantages of the invention may be better realised if the dressing is an island dressing, which is to say that the wound contact pad does not extend to any edge of the backing material. There may be a border of at least 0.1 cm or 0.5 cm or even at least 1 cm. This helps give better isolation of the wound from the environment.

Dressings in accordance with the invention will most preferably be sterile.

Various exemplary embodiments of the invention will now be described.

PREPARATION 1

Manufacture of Calcium Alginate Fibre 6.6 kg (6.0 kg bone dry) of sodium alginate powder was dissolved in 100 dm$^3$ of demineralised water containing sodium hypochlorite (60 g available chlorine) using a high speed stirrer. The excess chlorine is reduced to 25 ppm by the addition of sodium sulphite and the resultant solution was filtered to remove incompletely dissolved material. The solution was then spun through a viscose type spinning jet into a spin bath containing 1% calcium chloride and a sufficient quantity of cetyl pyridinium chloride (a quaternary ammonium wetting agent) to prevent fibre adhesion. After stretching the fibres in a steam chamber, the yarn is washed free from spin bath liquors in a conventional wash bath system, dried and collected either in a box or on a cheese winder.

PREPARATION 2

Manufacture of 80:20 Ca:Na Fabric 26.875 kg of calcium alginate tow from the spinning machine (equivalent to 21.5 kg bone dry alginate; defined as 100 equivalents) as prepared in Preparation 1 was placed in a stainless steel centrifuge equipped with a sump tank and a pump to recirculate the liquors through the fibres. 190 dm$^3$ of water were added to the sump tank and pump started with the centrifuge slowly revolving. 2 dm$^3$ of concentrated hydrochloric acid were slowly added to the water which were circulated for 10 minutes. The liquor was titrated against EDTA to measure its calcium content. Small additions of hydrochloric acid were made until the calcium content of the liquors corresponded to 20% removal of the calcium originally present in the fibres (20 equivalents). The liquor is then run to drain and the fibre washed with fresh water until no acidity is detectable in the runnings.

The sump tank is filled with 200 dm$^3$ of 50/50 v/v industrial methylated spirits (IMS)/water. Neutralisation is effected by circulating this liquor through the fibres and slowly adding 800 g of sodium hydroxide dissolved in 50/50 v/v IMS/water, taking care that the pH does not rise above 9.0. On completion of neutralisation a sample of the yarn gives no residual acidity.

The tow is washed in 80% v/v IMS/water and then in pure IMS; it is centrifuged as dry as possible and then dried in air at 40° C. The tow is then crimped, staple cut and converted to non-woven fabric by a conventional carding, cross-lapping and needle punching technique.

PREPARATION 3

First Alternative Manufacture of 80:20 Ca:Na Fabric

Calcium alginate tow as prepared in Preparation 1, is crimped, staple cut and converted to non-woven fabric by a conventional carding cross-lapping needle punching technique. 4 kg of calcium alginate fabric (3.2 kg bone dry) were placed in a miniature winch dyeing machine constructed of stainless steel. The winch was filled with the solution consisting of 2 kg sodium hydroxide, 4.7 kg glacial acetic acid, 10 dm$^3$ of IMS and made up to 100 dm$^3$ with water. After winching for 30 minutes the liquor is drained, and the fabric washed free of acetate liquor with successive amounts of 8% v/v IMS/water. The fabric is then air dried.

PREPARATION 4

Second Alternative Manufacture of 80:20 Ca:Na Fabric

Calcium alginate fibres, which are commercially available and may have been spun from a 40,000 hole jet, are fed into a bath containing sodium carbonate solution at approximately 0.5N (26.5 g/dm$^3$ as anhydrous Na$_2$CO$_3$). The bath is well agitated by means of a recirculation pump, and the yarn is allowed to lie in the bath for about 30 seconds. To prevent fibre adhesion, acetone (10% w/v) is present in the bath. The fibres are then washed in increasing concentrations of acetone/water before being squeezed dry and dried in a through-air drier. The resulting fibres contained calcium and sodium ions in an 80:20 equivalent basis and were converted to a non-woven fabric as described in preparation 3.

Calcium carbonate precipitated in the course of the reaction finds its way into a sump tank in the agitation pump circuit and is easily removed at the completion of the reaction.

PREPARATION 5

Third Alternative Manufacture of 80:20 Ca:Na Fabric 25.8 kg of calcium alginate fibre are placed in a centrifuge the outlet of which runs into a tank fitted with a pump which recirculates the liquor through the fibre in the drum. 100 liters of water are added to the tank, the pump is started and the drum slowly rotated. Sufficient hydrochloric acid is added to the liquor to remove 20% of the calcium present in the fibre. Since the initial calcium alginate in the fibre was 21.5 kg, bone dry, i.e. 100 equivalents, it is necessary to remove 20 equivalents of calcium. The theoretical quantity of hydrochloric acid is 2 liters, but in practice, due to the reverse reaction of the calcium ions in the liquors considerably more than this quantity of acid is required. The calcium in the liquor is determined by EDTA titration. When the desired quantity has been removed to the liquor, the liquors are drained and the fibre washed with water until free of acid. The centrifuge is then spun to full speed to remove as much water as possible. The yarn is then neutralised using a solution of 100 liters of 20% w.w. acetone/water containing 1060 g of anhydrous sodium carbonate which is circulated by means of the pump through the fibre in the slowly rotating drum. These liquors are displaced by 50% w.w. acetone water and finally washed at full speed of the centrifuge with pure acetone. The fibre obtained consists of 80:20 calcium sodium alginate and was converted to a non-woven fabric as described in preparation 3.

PREPARATION 6

Fourth Alternative Manufacture of 80:20 Ca:Na Fabric

An alginate tow (size 60,000 d.tex) spun by a conventional spinning machine is washed by water in a conventional tow washer to remove spin bath liquors. The wet tow is then pressed at 10 m per minute through a 1 m bath containing approximately N/10 hydrochloric acid and then through a second water wash. The strength of the acid and the residence time of the yarn in the acid bath are regulated so that the titre of a length of yarn of known weight corresponds to 20% presence of acid groups. The titration is done in water against caustic soda using phenol phthalein as indicator. The acid tow is then passed through a 3 m bath containing approximately 10% of acetone and a mixture of sodium carbonate and bicarbonate, provided by adding sodium carbonate. The composition of this bath is controlled by titration against HCl/phenol phthalein so that the final yarn shows neither residual acid nor residual alkali. The yarn coming from this bath is washed in increasing strengths of acetone/water solutions to remove free inorganic salts. The yarn is allowed to soak in the last bath for about 5 minutes before squeezing out the liquor. Then the yarn is dried in air in the normal manner and was converted to a non-woven fabric as described in preparation 3.

EXAMPLE 1

A backing layer was prepared in accordance with Example 1 of GB-A-1280631, and a pad of calcium:-sodium alginate fabric as produced in Preparation 2 was applied to the backing material to form an island dressing. A silicone release paper was applied to the adhesive surface and the alginate pad, and the dressing was sterilised by gamma irradiation.

EXAMPLE 2

A backing layer was prepared in accordance with Example 1 of GB-A-1280631, and a pad of calcium:-sodium alginate fabric as produced in Preparation 3 was applied to the backing material to form an island dressing. A silicone release paper was applied to the adhesive surface and the alginate pad, and the dressing was sterilised by gamma irradiation.

EXAMPLE 3

A sample of the product sold by Smith & Nephew under the trade mark OPSITE was purchased for use as a backing layer. This product is understood to be within the general teaching of GB-A-1280631. A pad of calcium:sodium alginate fabric as produced in Preparation 2 was applied to the backing material to form an island dressing. A silicone release paper was applied to the adhesive surface and the alginate pad, and the dressing was sterilised by gamma irradiation.

EXAMPLE 4

A sample of the product sold by Smith & Nephew under the trade mark OPSITE was purchased for use as a backing layer. This product is understood to be within the general teaching of GB-A-1280631. A pad of calcium:sodium alginate fabric as produced in Preparation 3 was applied to the backing material to form an island dressing. A silicone release paper was applied to the adhesive surface and the alginate pad, and the dressing was sterilised by gamma irradiation.

EXAMPLES 4 and 5

The procedures of Examples 3 and 4 were repeated, except that for the backing layer a semipermeable adhesive copolymer film obtained from DRG under the Trade Mark MEDIFIX 6013 was used. The film was suitable for making dressings in accordance with Specification 37 of the Drug Tariff (HMSO) and had the following characteristics:

| | |
|---|---|
| Dry weight: | 14 $g/m^2$ |
| MVTR | 624 $g/m^2/24$ hr |
| Adhesion (pre-irradiation) | >1.0 kg/25 mm |
| Tensile strength | 0.38 kg/cm |
| Elongation | 600% |
| Weight of adhesive mass | 25-35 $g/m^2$ |
| Elastic modulus | 2.04 N/cm. |

After the island dressing was prepared, it was sealed into a clear envelope and sterilised by gamma irradiation. The adhesion was again measured and found to be 0.43 kg/25 mm.

I claim:

1. A wound dressing comprising a backing layer and a wound contact pad, wherein the wound contact pad comprises mixed calcium and sodium cation alginate fibres, the equivalent ratio of the calcium to sodium cations being about 80:20.

2. A wound dressing as claimed in claim 1, wherein the pad is a non-woven sheet of alginate fibres.

3. A wound dressing as claimed in claim 1, wherein the alginate fibers comprise a ratio of guluronate/mannuronate residues in the ranges of from 1.5:1 to 2.5:1.

4. A wound dressing as claimed in claim 1, wherein the pad includes one or more antimicrobial agents and/or one or more local anaesthetics.

5. A wound dressing as claimed in claim 1, wherein the backing layer is a semi-permeable material.

6. A wound dressing as claimed in claim 1, wherein the wound contact pad does not extend to the edges of the backing layer.

* * * * *